United States Patent
De Siqueira

Patent Number: 5,284,441
Date of Patent: Feb. 8, 1994

[54] PRECISION DEVICE FOR ATTACHING REMOVABLE DENTAL PROSTHESIS

[76] Inventor: Luis A. De Siqueira, Rua Lauro Muller, 66 apto. 402, Botafogo, 22290-Rio de Janeiro, Brazil

[21] Appl. No.: 838,211
[22] PCT Filed: Jul. 8, 1991
[86] PCT No.: PCT/BR91/00012
   § 371 Date: Apr. 28, 1992
   § 102(e) Date: Apr. 28, 1992
[87] PCT Pub. No.: WO92/00704
   PCT Pub. Date: Jan. 23, 1992

[30] Foreign Application Priority Data
   Jul. 9, 1990 [BR] Brazil ............... PI/9003271

[51] Int. Cl.⁵ ............................................. A61C 13/12
[52] U.S. Cl. ..................................... 433/181; 433/177
[58] Field of Search ................ 433/169, 177, 181, 182, 433/183, 190

[56] References Cited

U.S. PATENT DOCUMENTS

| | | | |
|---|---|---|---|
| 2,347,340 | 4/1944 | Smallen | 433/177 |
| 4,293,303 | 10/1981 | Dalla Bona | 433/177 |
| 4,634,380 | 1/1987 | Zahn | 433/181 |
| 4,659,312 | 4/1987 | Bademis | 433/182 |
| 4,698,020 | 10/1987 | Menicacci | 433/177 |
| 4,768,957 | 9/1988 | Segura | 433/181 |
| 4,815,973 | 3/1989 | Jansen | 433/181 |
| 5,030,094 | 7/1991 | Nardi et al. | 433/169 |

FOREIGN PATENT DOCUMENTS

| | | |
|---|---|---|
| 199961 | 6/1968 | Brazil . |
| 7704662 | 3/1978 | Brazil . |
| 845239 | 7/1952 | Fed. Rep. of Germany . |
| 1566193 | 4/1970 | Fed. Rep. of Germany . |
| 1033858 | 7/1953 | France . |
| 355253 | 8/1961 | Switzerland . |

*Primary Examiner*—John J. Wilson
*Attorney, Agent, or Firm*—Cushman, Darby & Cushman

[57] ABSTRACT

Patent of invention of a precision device for attaching removable dental prosthesis, designed for the upper and lower dental arch free ends, consisting of a fixed male member and a removable female member, capable of absorbing, when engaged through an overlapping movement, all masticatory force due to gingival occlusive movement and therefore transferring it in a distributed manner over the mucous membrane on which the removable prosthetic portion is seated, this effect being cause by a dampening element located in the male member, member being made of a rigid material, of little thickness, formed in an approximately rectagular shape, there being two cavities on one of its faces and there being another cavity on the other face, there being, joined to cavity, a slit which engages spring inside said cavity; member consists also of a hollow rigid material piece, whose inner shape is the same as member there being on the inner walls of said member two pins and a recurved pin, positioned so that, during overlapping movement for engagement, pin engages cavity recurved pin engages through pressure spring and pin engages cavity respectively.

11 Claims, 4 Drawing Sheets

PRECISION DEVICE FOR ATTACHING REMOVABLE DENTAL PROSTHESIS

BACKGROUND OF THE INVENTION

The present invention relates to a precision device for attaching removable dental prothesis specially designed for the upper and lower dental arch free ends. The device is responsible for interlocking the removable prosthetic portion to a support tooth.

A prothesis with a device of this kind is disclosed in the Brazilian Patent document PI 199961 which provides a male fitting member and a female fitting member of a cylindrical cross-sections, the former being implanted in the natural tooth adjacent to a dental arch defect which is intended to be filled and the latter member being fastened to a lateral face in the movable prosthetic portion. The movable portion is vertically inserted, so that the female member fits on the male member. There is also provided in each member a vertical slot that allows pressure adjustments when both members are fitted together.

The Brazilian Patent document PI 7704662 describes a dental prothesis which can substitute for the movable bridge's clamp. The apparatus is also composed of a male member and a female member of a rectangular cross-sections, vertically fitting together.

An alternative construction for the above mentioned prothesis is provided in another Brazilian Document PI 8606582, which describes an apparatus comprising the preparation of one or more support crowns associated with the male member of a locking system, which consists of a fitting box provided with a hole having a narrower opening in its upper portion. The other portion of the apparatus is removable, consisting of a double bar metal base. The base is associated with the female member of a locking system. The female member is provided with a lock pin, where it is adapted to a receiving hole in the male member.

Other fittings of this kind are known through U.S. Pat. No. 4,634,380 and 4,768,957, German 3,419,144 and Swiss 649,209, which are primarily fittings consisting of male and female members of various shapes, being provided with a lock pin. When these fittings are used for attaching a removable portion in the dental arch free ends to a support tooth, they need stabilizer metal bars, which cross-over the palate or the mouth's lingual portion, from side to side.

U.S. Pat. No. 4,698,020, Swiss 579,387 and 644,483 and French 7,922,160 refer to fittings with similar features to the above mentioned, but have differences as to the attachment of the removable portion to a fixed portion. The kind of attachment used in these fittings is made by pressure during fastening, which is caused by a spring whose only purpose is to provide a more precise and secure attachment.

All existing removable precision prosthetic apparatuses, when used on free ends, present serious clinical and aesthetic problems such as loss of mucous membrane sensitivity, gingivitis, annoyance during adaptation, causing marks on the mucous membrane, acidity, and other problems, due to the devices used in the apparatus for attaching a removable prosthetic portion to a fixed prosthetic portion.

Besides the above mentioned drawbacks, it should be noted that these devices have no retention features of their own from the apparatus' movable portion to the fixed portion thereof and none for distributing and balancing the side forces occurring during mastication. Thus, stabilizing bars are needed in order to compensate such problems and to provide a greater strength to the apparatus as well.

In an attempt to solve these problems, Brazilian Patent Document PI 8606582 uses an elastic connection system developed to join a saddle to the other components of a partial removable prothesis, through non-rigid mechanisms that allow some freedom of controlled and independent movements for the connecting element.

This kind of non-rigid mechanism, made of metal bars having a greater coefficient of elasticity than the support elements and the periodontal ligament fibers of pilar teeth, allows the side forces imposed on the very support teeth to be minimized.

However, these elastic bars cannot effectively solve the masticatory force distribution on the mucous membrane. Most of the force concentration is shown to fall directly on the retention teeth, which causes an unfitting mastication movement, technically called deocclusion, and teeth mobility, causing headaches, ear pain and lacrimation in the patent. Such effects and the very own bar cause several of the above mentioned clinical and aesthetic problems.

Regarding the elastic property provided to such bars, its action is not effective, since its effect is impaired by their anatomical configuration, having a flat and inclined shape, in accordance with the osseous slope anatomy of the mandible lingual face's mucous membrane, therefore not allowing the elastic action to absorb the masticatory force.

SUMMARY OF THE INVENTION

In order to suppress the causes of the problems and drawbacks disclosed by already existing apparatuses, a precision device was made for attaching a removable dental prothesis specially designed for the upper and lower dental arch free ends, needing no kind of elastic bars, stabilizer bars or clamps. The apparatus is able to absorb through a damper element contained therein all masticatory forces due to gingival occlusive movement and therefore, and transfer the forces in a distributed manner over the mucous membrane where the removable prosthetic portion is seated. The dampening effect provides greater stability for the removable piece on the mucous membrane and stability is also enhanced by a more precise engagement between the movable female member and the fixed male member.

Through the present invention, it was verified that, surprisingly, the engagement precision and the dampening element existing in the device provide a mechanism technically called "force breaking", capable of preventing the masticatory force to be transferred to retention teeth, thus preventing the teeth from having mobility and becoming disarticulated.

Besides these improvements, the device provides an aesthetically true appearance for the movable prosthetic portion, giving the impression 30 that the same represents the patent's natural teeth, allowing an even greater freedom of movement for the tongue, insertion and removal, with an easy access and handling of the movable prosthetic portion.

BRIEF DESCRIPTION OF THE DRAWINGS

The invention will be described in greater detail in the following, with reference to an embodiment represented in the drawings.

DETAILED DESCRIPTION OF THE PRESENTLY PREFERRED EXEMPLARY EMBODIMENTS

Figure 1A:
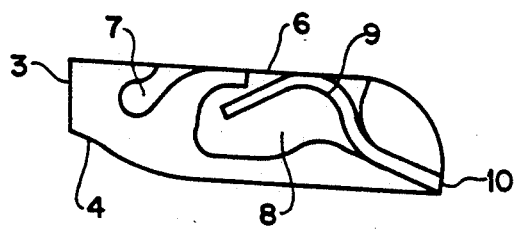
FIGS. 1A-1F are views of the elements composing the device for attaching removable dental prothesis according to the invention.
Figure 1B:
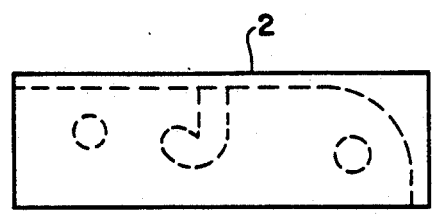
Figure 1C:
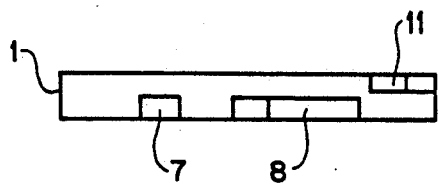
Figure 1D:
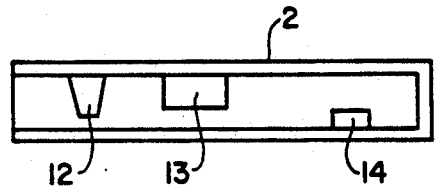
Figure 1E:
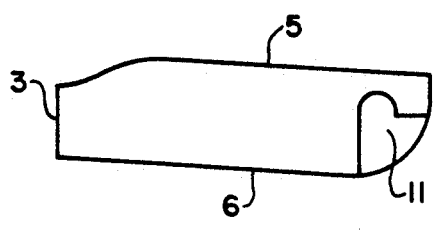
Figure 1F:
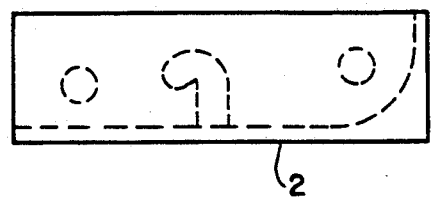
Figure 2:
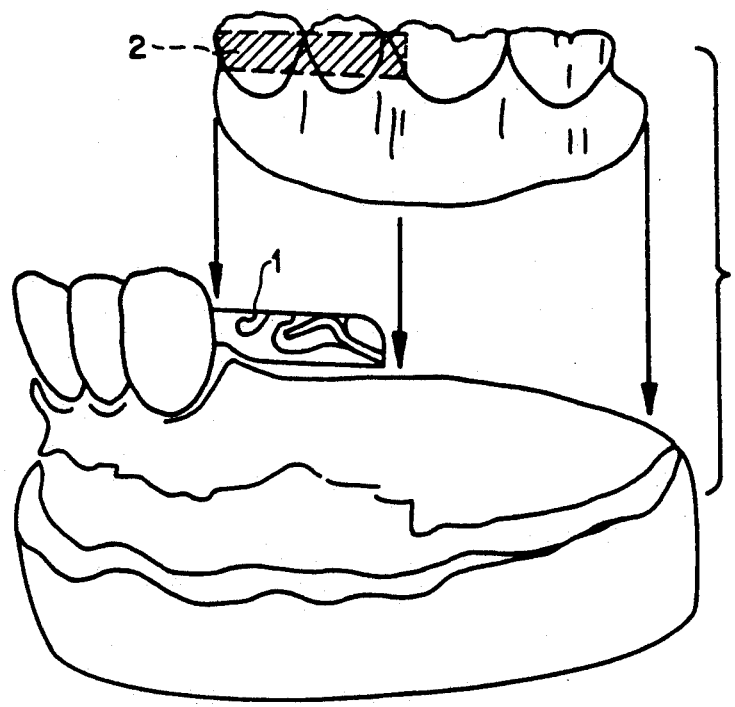
FIG. 2 is a schematic and exploded view of the coupling of elements composing the device, mounted on retention teeth and on the removable prosthetic piece.

The present invention relates to a precision device consisting of a male member (1) and a female member (2) engaged with each other through an overlapping movement.

According to FIGS. 1A-1F, the male member (1) is a metal alloy piece, preferably from nobel metal, formed in various shapes, approximately rectangular, or having little thickness, and having its design defined by forming a reduced dimension edge (3) as a function of the concave curve (4) formed by edge (5) as it joins edge (3). In this manner, edge (6) is joined to edge (3) at one end. The other end of edge (6) is joined to edge (5), forming a convex curve.

Figure 3:
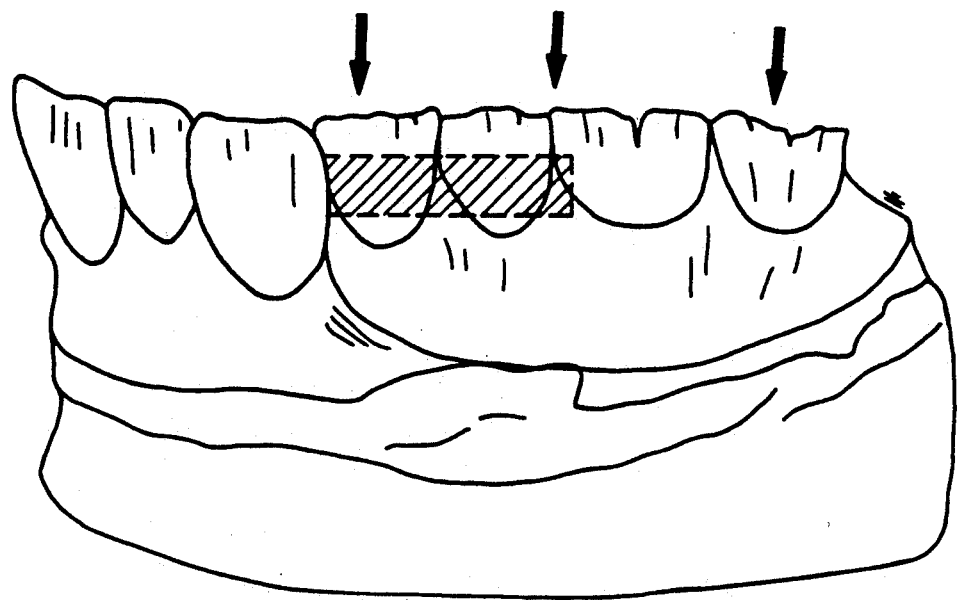
FIG. 3 is a schematic view of the coupling of male and female members on retention teeth and on the removable prosthetic piece, respectively.
Figure 7:
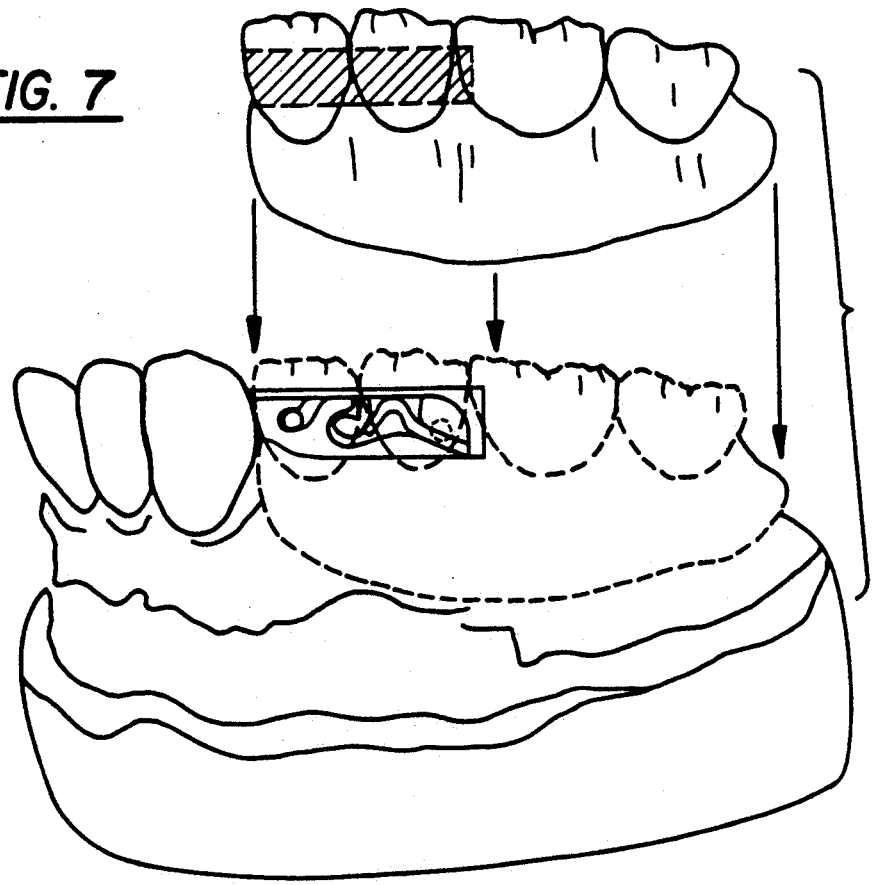
FIG. 7 is a schematic view of the device shown being coupled to retention teeth.

The male piece (1) has in its face toward the mouth's labial side, two cavities (7) and (8), of curved shape, cavity (7) being located near edges (3) and (6) and cavity (8) approximately located in the face's center. Cavities (7) and (8), in addition to fitting and attaching the female member (2) to the male member (1), have a further function. Cavity (7) supports member (2), avoiding its rising, and cavity (8) dampens the masticatory force exerted on member (2), which in turn acts on member (1). The coupling of the male member (1) and female member (2) is shown in FIGS. 3 and 7.

This dampening effect is caused by an element consisting of a metal spring (9) which in turn is a continuation of cavity (8). The other face member (1) is located in another cavity (11) near the curve formed by edges (5) and (6); the function of the cavity being to prevent longitudinal displacement and therefore loosening of member (2) when making a protruding movement between dental arcs.

According to FIGS. 1A-1F and 2, the female member (2), through overlapping, engages precisely over the male member (1), so that member (1) couples to member (2) in a just and precise manner.

Member (2) is also a metal hollow piece, whose inner shape is the same as member (1); there being in the inner walls of member (2) two pins (12), (14) and a hook-shaped pin (13), positioned so as, during overlapping for engagement of member (2) to member (1), pin (12) engages cavity (7), hook-shaped pin (13) engages through pressure spring (9) and pin (14) engages cavity (11), respectively. It should be noted that the fact that cavity (8) is located in the faced member (1) toward the mouth's labial portion is due to the possibility of an easier replacement of spring (9), when needed.

Figure 4:
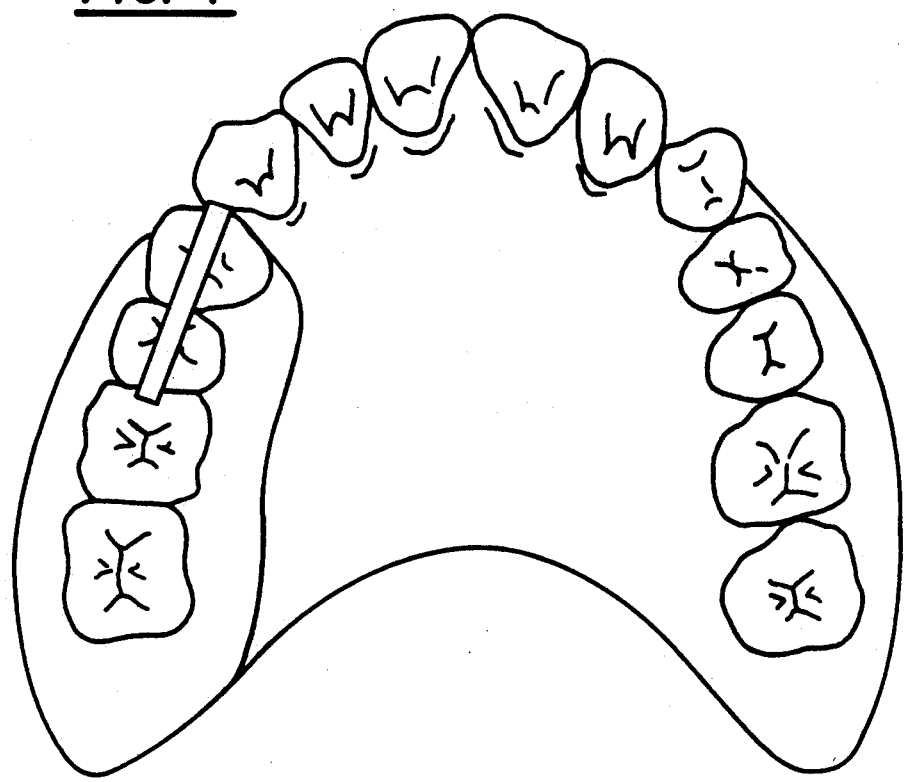
FIGS. 4-6 are upper frontal views of alternative constructions of removable prothesis for free ends.
Figure 5:
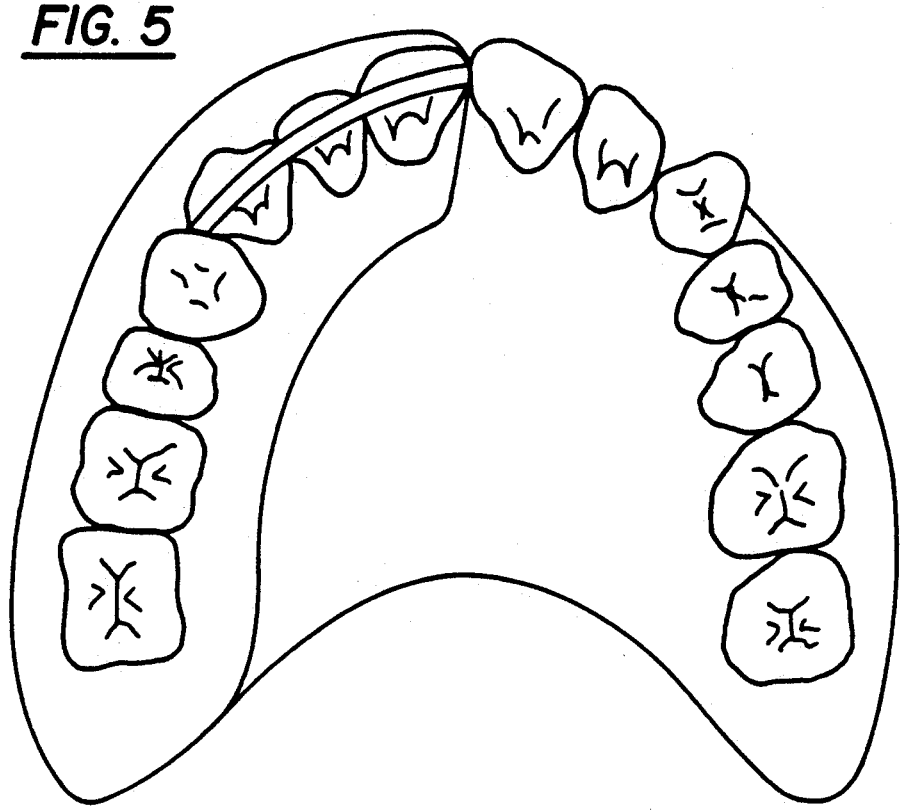
Figure 6:
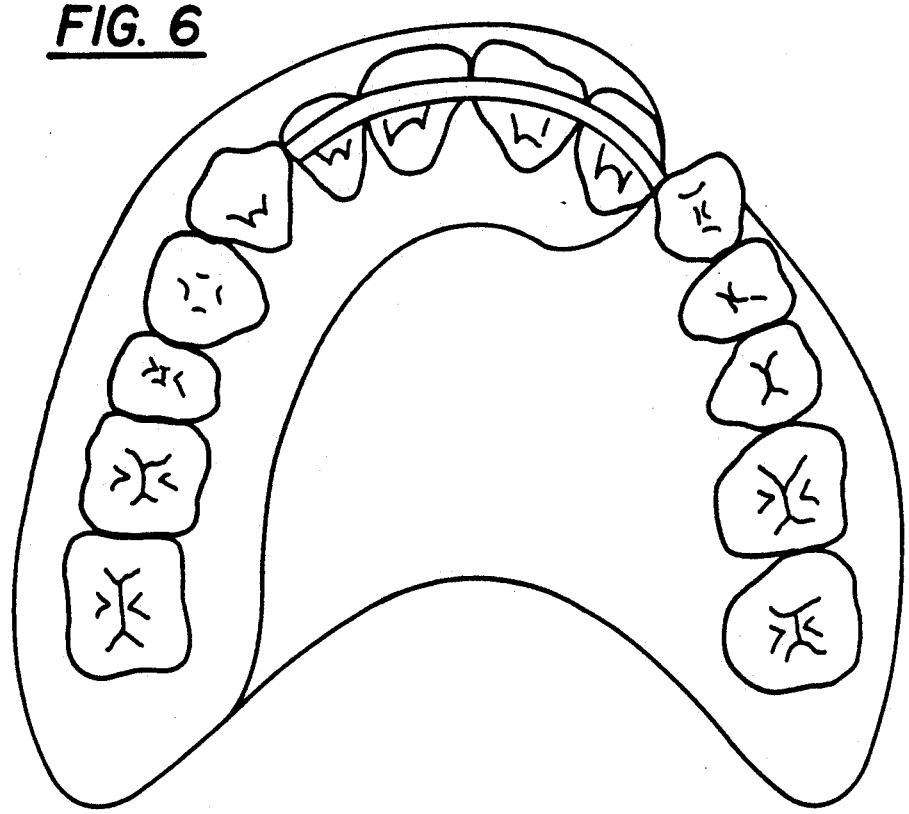

According to FIGS. 4-6 an alternative embodiment of the device's shape regarding its longitudinal axis is presented as straight (FIG. 4) semi-curved (FIG. 5) and curved shape (FIG. 6).

The dampening element may further consist of a rubber spring or any adequate elastic material.

The arrangement illustrated in the Figures relates only to an example of realization, the present invention being limited only to the following claims.

I claim:

1. A device for precisely attaching removable dental prothesis for upper and lower dental arch free ends comprising:
    a male member; and
    a female member;
    one of said male and female members being fastened to at least one retaining tooth, the member not fastened to the support tooth being fastened to the prothesis,
    one of said male and female members including a damping member for dampening chewing forces exerted on the prothesis and said retaining tooth when said male member is coupled to said female member, said dampening member having means for distributing all chewing forces over the mucosa surface of the mouth.

2. The device as claimed in claim 1, wherein said male member is fastened to said at least one retaining tooth, said female member being anchored to the prosthesis.

3. The device as claimed in claim 2, wherein each said male member and female member are composed of rigid material.

4. The device as claimed in claim 1, wherein said male member is of substantially rectangular form and includes:
    first and second edge portions;
    a concave curved portion defined between said first and second edge portions;
    a third edge joining said first edge; and
    a convex portion defined between said third edge and said second edge.

5. The device as claimed in claim 4, wherein said male member includes surfaces defining first and second cavities of curved shape, said cavities being defined in a face of said male member, said face being oriented toward a labial portion of the mouth, said cavities being disposed near said first and third edges, another face of said male member including a third cavity near said convex portion.

6. The device as claimed in claim 5, wherein said damping member includes a spring affixed at one end to a portion of said male member, a second end of said spring being disposed within said second cavity.

7. The device as claimed in claim 6 wherein said female member is of substantially hollow configuration having an inner shape so as to correspond to a shape of the male member, said female member including first and second pins and a third, hook-shaped pin,
    upon coupling said male member to said female member, said first pin engages said first cavity, said hook-shaped pin engages a portion of said second cavity, said hook-shape pin is biased against said portion by said spring, said second pin engages said third cavity.

8. The device as claimed in claim 7, wherein said spring is made from an elastic material.

9. The device as claimed in claim 1, wherein said male and female members are configured so as to form a straight member when coupled.

10. The device as claimed in claim 1, wherein said male and female members are configured so as to form a semi-curved member when coupled.

11. The device as claimed in claim 1, wherein said male and female members are configured so as to form a curved member when coupled.

* * * * *